United States Patent [19]

Ginsburg et al.

[11] Patent Number: 4,790,310

[45] Date of Patent: Dec. 13, 1988

[54] LASER CATHETER HAVING WIDE ANGLE SWEEP

[76] Inventors: Robert Ginsburg, 2489 Alpine Rd., Menlo Park, Calif. 94025; David F. Profitt, 1154 Madison, Santa Clara, Calif. 95050

[21] Appl. No.: 10,868

[22] Filed: Feb. 4, 1987

[51] Int. Cl.$^4$ .......................... A61N 5/01; A61N 5/06
[52] U.S. Cl. .................. 128/303.1; 128/398; 219/121.8; 219/121.85
[58] Field of Search ............. 128/303.1, 362, 395, 128/397, 398, 635, 664–667, 63–66; 219/121 L, 121 LU, 121 LV, 121 LW, 121 LT

[56] References Cited

U.S. PATENT DOCUMENTS

| | | | |
|---|---|---|---|
| 1,959,127 | 5/1934 | Duerme | 128/6 |
| 2,437,916 | 12/1943 | Greenwald | 128/665 |
| 3,762,400 | 10/1973 | McDonald | 128/6 |
| 3,870,036 | 3/1975 | Fiore | 128/6 |
| 4,418,688 | 12/1983 | Loeb | 128/6 |
| 4,502,468 | 3/1985 | Burgin | 128/3 |

FOREIGN PATENT DOCUMENTS

| | | | |
|---|---|---|---|
| 540806 | 1/1941 | United Kingdom | 128/6 |
| 8301893 | 6/1983 | World Int. Prop. O. | 128/303.1 |

OTHER PUBLICATIONS

Livesay et al. (1985) Herz 10:343–350.
Macruz et al. (1985) Lasers in Surgery and Medicine, 5:199–218.
Ginsburg et al. (1984) Clin. Cardiol., 7:54–58.
Ginsburg et al. (1985) Radiology, 156:619–624.
Takekawa et al. (1985) Nippon Acta Radiologica, 45:1167–1169.

Primary Examiner—Lee S. Cohen
Assistant Examiner—David Shay
Attorney, Agent, or Firm—Townsend & Townsend

[57] ABSTRACT

An improved laser catheter system includes a flexible catheter tube having proximate and distal ends. The distal end, which is intended for inserting into a patient's artery, is axially split into at least two segments. Optical waveguides extend the length of the catheter tube and terminate at the distal end, with at least one waveguide secured to each of the spreadable segments. A mechanism is provided for spreading the segments while the catheter is implaced in the patient. Conveniently, a balloon catheter may be used by inserting it into the lumen of the laser catheter so that the balloon tip lies within the spreadable segments. By then inflating the balloon, the spreadable segments are spread apart as desired.

15 Claims, 2 Drawing Sheets

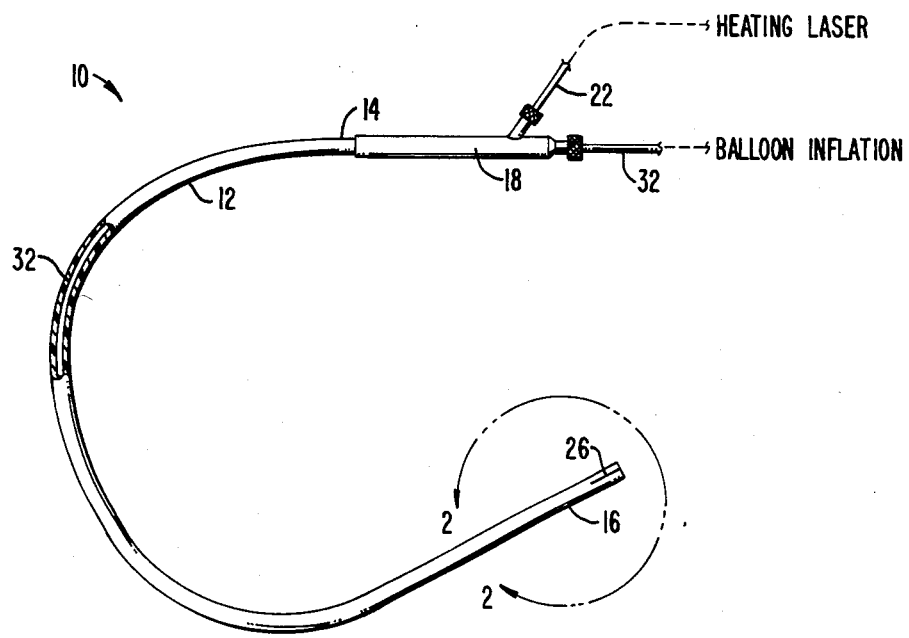
FIG.—1.
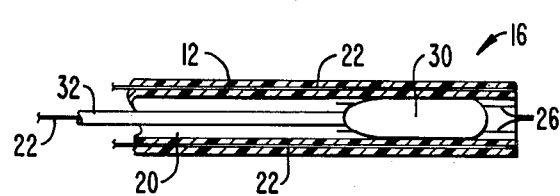
FIG.—2A.
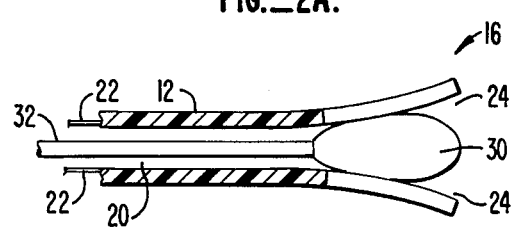
FIG.—2B.
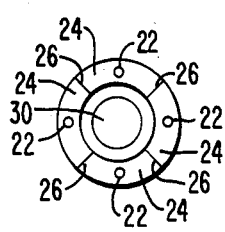
FIG.—3A.
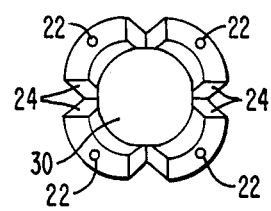
FIG.—3B.

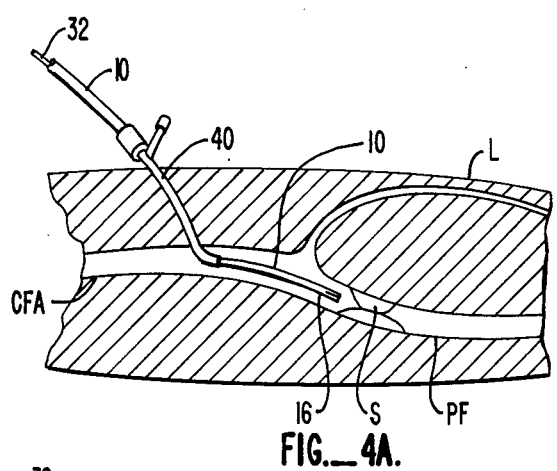
FIG._4A.
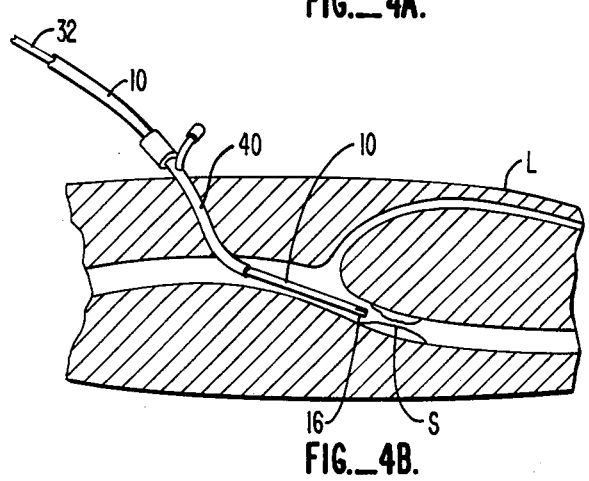
FIG._4B.
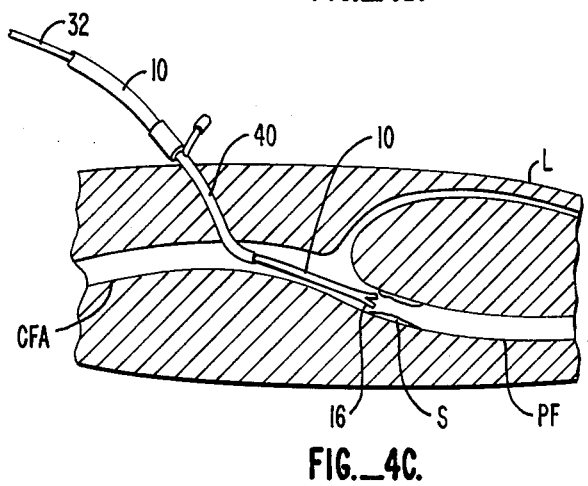
FIG._4C.

LASER CATHETER HAVING WIDE ANGLE SWEEP

BACKGROUND OF THE INVENTION

1. Field of the Invention

The present invention relates generally to apparatus and methods for the recanalization of stenosed arteries. More particularly, the invention relates to the use of laser catheters for the ablation of artherosclerotic plaque and thrombus.

Laser angioplasty relies on the use of optical fiber catheters to direct laser energy at arterial obstructions, such as plaque and thrombus. The technique has been used to remove obstructions from peripheral and coronary arteries. The catheters function by directing laser energy in a narrow, focused beam of light, typically having diameter of about 100–200 μm. The incident laser radiation heats and vaporizes the plaque, generally producing soluble by-products which are removed safely by the blood. The effect of the laser radiation, however, is generally limited to a path having in diameter approximately equal to that of the laser beam. Thus, sufficient opening of the obstructed region of the artery is not always achieved.

It would therefore be desirable to provide apparatus and methods for using lasers to open relatively wide channels through arterial obstructions. In particular, it would be desirable to provide laser catheters capable of sweeping laser beam(s) across an arterial obstruction to ablate a relatively wide area.

2. Description of Prior Art

Livesay et al. (1985) Herz 10: 343–350 and Macruz et al. (1985) Lasers in Surgery and Medicine 5: 199–218 are review articles describing the state of the art in laser angioplasty. Ginsburg et al. (1984) Clin. Cardiol. 7: 54–58 and Ginsburg et al. (1985) Radiology 156: 619–624 describe case studies where laser angioplasty has been used to open stenosed regions in the peripheral arteries. Takekawa et al. (1985), Nippon Acta Radiologica 45: 1167–1169 describes the combination of laser angioplasty and balloon angioplasty for opening stenosed regions of the iliac and femoral arteries. U.S. Pat. No. 4,418,688 describes a laser catheter employing a cable system for adjusting the alignment of the catheter tip.

SUMMARY OF THE INVENTION

The present invention provides a laser catheter system capable of simultaneously projecting a plurality of laser beams at an arterial obstruction. The use of multiple beams enhances plaque removal by simultaneously applying energy to a plurality of regions on the obstruction. Moreover, by sweeping the beams to different regions on the obstruction, additional portions of the obstruction may be removed.

The laser catheter system includes a flexible catheter tube having one end split axially into at least two spreadable segments, usually into at least four spreadable segments. Fiber optic waveguides extend axially through the tube, with at least one waveguide being attached to each spreadable segment. Conveniently, the waveguides will be disposed internally within the tube wall. Alternatively, the waveguides may be run in a bundle through the lumen of the tube and attached externally to the spreadable segments. A mechanism for spreading the segments is also provided. Conveniently, an inflatable balloon is located within the distal end of the catheter tube, although other mechanisms such as spreadable jaws might also be used.

The catheter system of the present invention functions by variably spreading the tube segments in order to direct the waveguides to different portions of the exposed face of the arterial obstruction. Usually, the segments will spread incrementally so the beams will remain focused at particular portions of the obstruction for a predetermined length of time. Allowing the beams to remain focused on a particular location allows sufficient time for the obstruction to be destroyed before the beam is moved to the next focus point. Additionally, the laser catheter may be moved axially within the arterial lumen in order to expose additional portions of the obstruction to the laser radiation. Using the apparatus and method of the present invention, substantially complete removal of arterial obstructions can be achieved.

BRIEF DESCRIPTION OF THE DRAWINGS

FIG. 1 illustrates a catheter constructed in accordance with the principles of the present invention.

FIG. 2A is a detailed view of the distal end of the catheter, shown in section.

FIG. 2B is a detailed view similar to FIG. 2A, except that the internal balloon has been inflated in order to spread the segments of the distal end.

FIG. 3A is an end view of the catheter of 2A.

FIG. 3B is an end view of the catheter of 2B.

FIGS. 4A–4C illustrate the method of the present invention as applied to clearing an obstruction of the profunda femoral artery in a leg.

DESCRIPTION OF THE SPECIFIC EMBODIMENTS

Referring now to FIG. 1, a laser catheter 10 constructed in accordance with the principles of the present invention will be described. The catheter 10 includes an elongate flexible tube 12 having a proximate and 14 and distal and 16. The proximate end 14 is connected to a manifold assembly 18 which in turn allows various external connections to be made to the catheter 10, as will be described hereinafter.

Referring now to FIGS. 1–3, the flexible tube 12 defines an interior lumen 20 (best observed in FIGS. 2A and 2B) and includes a plurality of axial waveguides 22 running its entire length. Preferably, the optical waveguides 22 are located integrally within the cylindrical wall of flexible tube 12. Alternatively, the waveguides may be routed through the lumen 20 and attached to the spreadable segments 24 in some other way. It is necessary that the waveguides run from the proximate end 14 (where they may be connected to a laser source) to the distal end 16, where they are somehow attached to the spreadable segments 24 so that the focii of the waveguides may be diverged by spreading said segments.

Spreadable segments 24 formed in the flexible catheter tube 12 by axially splitting the distal end 16. Split lines 26 are best observed in FIGS. 1, 2A, and 3A, and the configuration of distal end 16 after the segments have been spread is best observed in FIGS. 2B and 3B.

A mechanism for spreading the individual segments 24 while the catheter 10 is in place in an artery is provided. Conveniently, the mechanism comprises an inflatable balloon catheter 30 which is inserted into catheter 10 through the lumen 20. The balloon catheter 30 includes an inflation tube 32 which extends back to manifold 18 at proximate end 14 of the catheter 10. Inflation tube 32 is connected to a suitable pressurized inflation source, typically a pressurized source of saline or other physiologically-acceptable medium.

The materials of construction for the laser catheter system 10 are not critical. The flexible catheter 12 will typically be a physiologically-acceptable polymer, such as silicone rubber, natural rubber, polyvinyl chloride, polyurethane, polyester, or the like. Conveniently, the polymer will include substances which render the catheter radio-opaque so that it may be located by conventional imaging techniques. The balloon catheter 30 may be composed of similar polymers, with the balloon 30 itself typically being composed of a latex rubber. The waveguides 22 may be composed of any conventional fiber optic material, such as quartz or fused silicon, chosen to be compatible with the particular laser source chosen. Usually, the waveguide will be clad along its entire length although cladding unnecessary when the waveguide is internal to the wall of flexible tube 12.

A variety of suitable laser sources exists, including Argon lasers, carbon dioxide lasers, neodymium-YAG lasers, and the like. Preferred are lasers which lessen the possibility of perforation of the arterial wall.

The dimensions of the catheter are not critical. Typically, the catheter tube 12 will have a length in the range from about 50 to 100 cm, usually being about 75 cm, with an outside diameter in the range from about 4 to 8 French (Fr; 3 Fr=1 mm) and an inside (lumen) diameter in the range from about 3 to 6 Fr. The axial split lines 26 at the distal end 16 will have a length in the range from about 1 to 4 cm, typically being about 2 cm. The balloon catheter will have a length slightly greater than the catheter tube 12, typically being about 90 cm when the catheter 12 is about 75 cm. The outside diameter of the balloon 30 (uninflated) will usually be slightly less than the inside diameter of tube 12, and have a length slightly less than that of the splits 26. Typically, when the splits 26 are 2 cm, the balloon will have a length of about 1 cm.

Referring now FIGS. 4A-4C, the use of the laser catheter 10 of the present invention in clearing of an obstructions present in the femoral artery will be described. A sheath 40 is inserted into the patient's common femoral artery CFA according to conventional techniques, such as the Seldinger technique. After administering heparin or other suitable anti-coagulant, a guidewire (not illustrated) is inserted through the sheath 40 and guided to the region of stenosis under fluoroscopic guidance. The catheter 10 is then inserted over the guidewire until the distal end 14 reaches the area immediately adjacent to the region of stenosis. After withdrawing the guidewire, the balloon catheter 30 is inserted until the balloon trip reaches the distal end 16.

The laser radiation may be then directed through the catheter 10 onto the region of stenosis S. Initially, the segments 24 will be left in their closed or collapsed state, as illustrated in FIGS. 2A and 3A. In this configuration, the laser beams are directed from the catheter 10 along lines parallel to the axis of the tube at its distal end 16. The region of stenosis cleared is thus limited initially to a region corresponding roughly to the pattern of the waveguides 22 in the catheter 10. After the laser beams have been directed at the stenosis regions for a sufficient time to clear the material in their path, the balloon 30 may be inflated partially to spread or diverge the individual segments 24, as illustrated in FIGS. 2B and 3B.

The number of segments 24 is not critical, but will be at least 2, more usually at least 4, and may be as many as 8 or more. The segments will be spread apart incrementally so that the angle of divergence will be increased in a step-wise fashion. The total angle of divergence from the axial direction may ultimately reach about 45°, usually being achieved in about 20 steps, more usually being achieved in about 10 steps.

Although the preferred procedure is to incrementally increase the spreading of the segments 24, in some cases it may be desirable to continually move the segments in and out. It has been found that such sweeping of the laser beams across stenosed regions can result in differential heating of the obstruction and possible fracture thereof. Caution is advised with such an approach, however, since the resulting fragments may cause harm to the patient.

If stenosed regions S are particularly lengthy, it may be desirable to repeat the above-described procedure one or more times by advancing proximate end 16 of catheter 10 further into the region S as the threshold of the region is moved backward.

As with all laser angioplastic procedures, care must be taken to avoid perforation of the artery. Keeping the catheter co-axially aligned with the artery under fluoroscopic guidance will usually be satisfactory. As a further measure, spectral feedback systems have been described which prevent firing of the laser if the detected spectral pattern indicates that no plaque is in front of the laser beam.

Although the foregoing invention has been described in some detail by way of illustration and example for purposes of clarity of understanding, it will be obvious that certain changes and modifications may be practiced within the scope of the appended claims.

What is claimed is:

1. A catheter system comprising:
   an elongate flexible tube having a proximate end and a distal end, said distal end being axially split into at least two spreadable segments;
   a plurality of optical waveguides, with at least one waveguide being secured to each segment of the flexible tube; and
   means for spreading the segments in order to radially diverge the waveguides.

2. A catheter system as in claim 1, wherein the means for spreading the segments includes a balloon located internally at the distal end of the tube and means for inflating the balloon.

3. A catheter system as in claim 2, wherein the means for inflating the balloon includes a flexible inflation tube extending to the proximate end of the flexible tube.

4. A catheter system as in claim 1, wherein the elongate flexible tube includes a tube wall and the optical waveguides are disposed axially with the tube wall.

5. A catheter system as in claim 1, wherein the flexible tube is axially split into at least four spreadable segments.

6. A catheter system comprising:
   an elongate flexible tube defining an internal lumen and having distal and proximal ends, said distal end being insertable into a blood vessel and being axially split into a plurality of spreadable segments;
   a plurality of optical waveguides, with at least one waveguide being disposed axially within each segment of the flexible tube;
   an inflatable balloon disposed within the lumen at the distal end; and means for inflating the balloon.

7. A catheter system as in claim 6, wherein the means for inflating the balloon is an inflation tube running from the balloon, through the lumen, and to the proximal end of the flexible tube.

8. A catheter system as in claim 6, wherein the waveguides are located integrally within the wall of the flexible tube.

9. A catheter system as in claim 6, wherein the flexible tube is composed of a radio opaque material.

10. A catheter system as in claim 6, wherein the flexible tube has a length of at least about 50 cm, an outside diameter from about 0.10 to 0.40 cm, and the axial splits are from about 0.5 to 4.0 cm in length.

11. A method for ablating an obstruction in a blood vessel, said method comprising:

inserting a catheter into the blood vessel proximate the obstruction, said catheter having a plurality of discrete optical waveguides arranged axially therein;

directing laser radiation through said waveguides onto the obstruction for a preselected time period; and diverging the waveguides by a preselected angle during at least a portion of the time period they are carrying the radiation, whereby the area of the obstruction exposed to the radiation is increased.

12. A method as in claim 11, wherein the step of diverging the waveguides comprises inflating a balloon within the catheter to force the waveguides apart.

13. A method as in claim 12, wherein the preselected angle is in a range from about 0° to 45°.

14. A method as in claim 11, wherein the catheter is inserted into a peripheral artery.

15. A method as in claim 11, wherein the catheter is inserted into the coronary artery.

* * * * *